United States Patent [19]

Ingram et al.

[11] Patent Number: 5,162,516

[45] Date of Patent: Nov. 10, 1992

[54] CLONING AND SEQUENCING OF THE ALCOHOL DEHYDROGENASE II GENE FROM ZYMOMONAS MOBILIS

[75] Inventors: Lonnie O. Ingram; Tyrrell Conway, both of Gainesville, Fla.

[73] Assignee: University of Florida, Gainesville, Fla.

[21] Appl. No.: 200,110

[22] Filed: May 31, 1988

[51] Int. Cl.$^5$ ............................................. C12N 15/12
[52] U.S. Cl. ..................................... 536/27; 435/6; 435/190; 435/26; 935/9; 935/60
[58] Field of Search .................. 935/9; 435/69.1, 70.2, 435/172.1, 190, 161; 536/27

[56] References Cited

U.S. PATENT DOCUMENTS 5,000,000 3/1991 Ingram et al. ..................... 435/161

OTHER PUBLICATIONS

T. Conway, G. W. Sewell, Y. A. Osman, and L. O. Ingram, k"Cloning and Sequencing of the Alcohol Dehydrogenase II Gene from *Zymomonas mobilis*" J. Bacteriol. 169(6) 1987 pp. 2591-2597.
Conway, T., Y. A. Osman, J. I. Konnan, E. M. Hoffmann, and L. O. Ingram (1987) "Promoter and nucleotide sequences of the *Zymomonas mobilis* pyruvate decarboxylase," J. Bacteriol. 169:949-954.
Hoppner, T. C., and H. W. Doelle (1983) "Purification and kinetic characteristics of pyruvate decarboxylase and ethanol dehydrogenase from *Zymomonas mobilis* in relation to ethanol production," Eur. J. Appl. Microbiol. Biotechnol. 17:152-157.
Kinoshita, S., T. Kakizono, K. Kadota, K. Das, and H. Taguchi (1985) "Purification of two alcohol dehydrogenases from *Zymomonas mobilis* and their properties," Appl. Microbiol, Biotechnol. 22:249-254.
Montenecourt, B. S. (1985) "Zymomonas, a unique genus of bacteria," pp. 261-289 in A. L. Demain and N. A. Solomon (eds.), *Biology of industrial microorganisms,* Benjamin-Cummings Publishing Co., Menlo Park, CA.
Neale, A. D., R. K. Scopes, J. M. Kelly, and R. E. H. Wettenhall (1986) "The two alcohol dehydrogenases of *Zymomonas mobilis:* purification by differential dye ligand chromatography, molecular characterization and physiological role," Eur. J. Biochem. 154:119-124.
Scopes, R. K. (1983) "An iron-activated alcohol dehydrogenase," FEBS Lett. 156:303-306.
Wills, C., P. Kratofil, D. Londo, and T. Martin (1981) "Characterization of the two alcohol dehydrogenases of *Zymomonas mobilis,*" Arch. Biochem. Biophys. 210:775-785.

*Primary Examiner*—Esther L. Kepplinger
*Assistant Examiner*—Carol Bidwell
*Attorney, Agent, or Firm*—Saliwanchik & Saliwanchik

[57] ABSTRACT

The alcohol dehydrogenase II gene from *Zymomonas mobilis* has been cloned and sequenced. This gene can be expressed at high levels in other organisms to produce acetaldehyde or to convert acetaldehyde to ethanol.

1 Claim, 9 Drawing Sheets

```
                                                              -250
                                                                *
  1 AAAGGCAAAATCGGTAACCACATCTCAATTATTAAACAATACTTCATAATAAAAGACAACTTTTCATAATTTGCATAAGTCTTGATGTAAAAAATACA

-100
                                                                *
101 TATTTAGAAAGAACAAGCAGCCTTGCTCATCACCGCTGTCGCCGAGTAGAAAAATCTCGGCTTTCAGAAAAGAGGCCGCTTCGTTAAACAGACTATAAAT
                                                                            >P₁ Zm

1
                                                                *
201 GTGCTGGAATAAAGCGAACCCCTTGATCTGATAAACTGATAGACATATTGCTTTGCGCTGCCCGATTGCTGAAAATGCGTAAAAGGTGATTTTACTCG
                                                                                      >P₂ Zm, Ec

100
                                                                *
301 TTTTCAGGAAAAACTTTGAGAAAAACGTCTCGAAAACGGATTAAACGCAAAACAATAGAAAGGCGATTTCGCGAAAATGGTTGTTTCGGGTTGTTGCT

200
                          S.D.                                  *
401 TTAAACTAGTATGTAGGGTGAGGTTATAGCT ATG GCT TCT TCA ACT TTT TAT ATT CCT TTC GTC AAC GAA ATG GGC GAA GGT
                                  fMet Ala Ser Ser Thr Phe Tyr Ile Pro Phe Val Asn Glu Met Gly Glu Gly
```

Figure 2-1

```
                                          250                                               300
                                           *                                                 *
TCG CTT GAA AAA GCA ATC AAG GAT CTT AAC GGC AGC GGT TTT AAA AAT GCG CTG ATC GTT TCT GAT GCT TTC ATG AAC
Ser Leu Glu Lys Ala Ile Lys Asp Leu Asn Gly Ser Gly Phe Lys Asn Ala Leu Ile Val Ser Asp Ala Phe Met Asn
               *                                         350                                               *
AAA TCC GGT GTT GTG AAG CAG GTT CTG GAC CTG TTG AAA GCA CAG GGT ATT AAT TCT GCT GTT TAT GAT GGC GTT ATG
Lys Ser Gly Val Val Lys Gln Val Leu Asp Leu Leu Lys Ala Gln Gly Ile Asn Ser Ala Val Tyr Asp Gly Val Met
                     400                                                           450
                      *                                                             *
CCG AAC CCG ACT GTT ACC GCA GTT CTG GAA GGC CTT GGT CTT AAG ATC CTG AAG GAT AAC TCA GAC TTC GTC ATC TCC CTC
Pro Asn Pro Thr Val Thr Ala Val Leu Glu Gly Leu Gly Leu Lys Ile Leu Lys Asp Asn Ser Asp Phe Val Ile Ser Leu
                                         *                                    500                                  *
GGT GGT TCT CCC CAT GAC TGC GCC AAA GCC ATC GCT CTG GTC GCA ACC AAT GGT GGT GAA GTC AAA GAC TAC GAA
Gly Gly Ser Pro His Asp Cys Ala Lys Ala Ile Ala Leu Val Ala Thr Asn Gly Gly Glu Val Lys Asp Tyr Glu
                              550                                                          600
                               *                                                            *
GGT ATC GAC AAA TCT AAG AAA CCT GCC CTG CCT TTG ATG TCA ATC AAC ACG GCT GGT ACG GCT TCT GAA ATG ACG
Gly Ile Asp Lys Ser Lys Lys Pro Ala Leu Pro Leu Met Ser Ile Asn Thr Ala Gly Thr Ala Ser Glu Met Thr
```

Figure 2-2

```
                                                                              650
      *               *                *                  *        *
CGT TTC TGC ATC ATC ACT GAT GAA GTC CGT CAC GTT AAG ATG GCC ATT GTT GAC CGT CAC GTT ACC CCG ATG GTT TCC
Arg Phe Cys Ile Ile Thr Asp Glu Val Arg His Val Lys Met Ala Ile Val Asp Arg His Val Thr Pro Met Val Ser
          700                                                          750
           *                *               *                 *                *
GTC AAC GAT CCT CTG TTG ATG GTT GGT ATG CCA AAA GGC CTG ACC GCC GCC ACC GGT ATG GAT GCT CTG ACC CAC GCA
Val Asn Asp Pro Leu Leu Met Val Gly Met Pro Lys Gly Leu Thr Ala Ala Thr Gly Met Asp Ala Leu Thr His Ala
                                800                                                          850
      *               *          *                  *                  *                      *
TTT GAA GCT TAT TCT TCA ACG GCA GCT ACT CCG ATC ACC GAT GCT TGC GCC TTG AAG GCG TCC ATG ATC GCT AAG
Phe Glu Ala Tyr Ser Ser Thr Ala Ala Thr Pro Ile Thr Asp Ala Cys Ala Leu Lys Ala Ser Met Ile Ala Lys
                                              900
          *                *                  *            *                  *
AAT CTG AAG ACC GCT TGC GAC AAC GGT AAG GAT ATG CCA GCT CGT GAA GCT ATG GCC CAA TTC CTC GCT GGT
Asn Leu Lys Thr Ala Cys Asp Asn Gly Lys Asp Met Pro Ala Arg Glu Ala Met Ala Tyr Ala Gln The Leu Ala Gly
```

Figure 2-3

```
*                                                               1000
ATG GCC TTC AAC AAC GCT TCG CTT GGT TAT GTC CAT GCT ATG GCT CAC CAG TTG GGC GGC TAC TAC AAC CTG CCG CAT
Met Ala Phe Asn Asn Ala Ser Leu Gly Tyr Val His Ala Met Ala His Gln Leu Gly Gly Tyr Tyr Asn Leu Pro His

1050
GGT GTC TGC AAC GCT GTT CTG CTT CCG CAT GTT CTG GCT GTT TAT AAC GCC TCT GTC GTT GCT GTT GCT GGT CGT CTG AAA GAC GTT
Gly Val Cys Asn Ala Val Leu Leu Pro His Val Leu Ala Val Tyr Asn Ala Ser Val Val Ala Val Ala Gly Arg Leu Lys Asp Val 1100                                                   1150
GGT GTT GCT ATG GGT CTC GAT ATC GCC AAT CTC GCT GAT AAA GAA GGC GCA GAA GCC ACC ATT CAG GCT GTT CGC GAT
Gly Val Ala Met Gly Leu Asp Ile Ala Asn Leu Ala Asp Lys Glu Gly Ala Glu Ala Thr Ile Gln Ala Val Arg Asp

1200
CTG GCT TCC ATT GGT ATT CCA GCA AAT CTG ACC GAG CTG GGT GCT AAG AAA GAA GAT GTG CCG CTT CTT GCT GAC
Leu Ala Ser Ile Gly Ile Pro Ala Asn Leu Thr Glu Leu Gly Ala Lys Lys Glu Asp Val Pro Leu Leu Ala Asp
```

Figure 2-4

```
                                                    1300
                                                      *
CAC GCT CTG AAA GAT GCT TGT GCT CTG ACC AAC CCG CGT GAT CAG AAA GAA GTT GAA GAA CTC TTC CTG AGC
His Ala Leu Lys Asp Ala Cys Ala Leu Thr Asn Pro Arg Gln Gly Asp Gln Lys Glu Val Glu Glu Leu Phe Leu Ser
                                                                      1400
                                                                        *
GCT TTC TAATTTCAAAACAGGAAAACGGTTTCCGTCCTGATTTCAAGCAAACAATGCCTCCGATTTCTAATCGGAGGCATTTGTTTTGTTTAT
Ala Phe ---
                              1450
                                *
TGCAAAAACAAAAAATATTGTTACAAATTTTACAGGCTATTAAGCCTACCGTCATAAATAATTTGCCATTT
```

CLONING AND SEQUENCING OF THE ALCOHOL DEHYDROGENASE II GENE FROM *ZYMOMONAS MOBILIS*

ACKNOWLEDGMENTS

This research was supported in part by the Florida Agricultural Experiment Station and by grants from the U.S. Department of Energy, Office of Basic Energy Research (FG05-86ER3574); the National Science Foundation (DMB 8204928); and the U.S. Department of Agriculture, Alcohol Fuels Program (86-CRCR-1-2134). We gratefully acknowledge the support of Y. A. Osman by the Egyptian Ministry of Higher Education.

We appreciate the excellent technical assistance of J. M. Neville during the construction and screening of M13 clones.

BACKGROUND OF THE INVENTION

In the obligately fermentative bacterium *Zymomonas mobilis*, the regeneration of NAD+ depends upon two enzymes, i.e., pyruvate decarboxylase (EC 4.1.1.1) and alcohol dehydrogenase (EC 1.1.1.1)(27, 37) *Z. mobilis* is the only known obligately fermentative procaryote which utilizes an Entner-Doudoroff pathway for glycolysis and, like *Saccharomyces cerevisiae*, produces ethanol and carbon dioxide as dominant fermentation products. We recently reported the sequence of the pyruvate decarboxylase gene from *Z mobilis* (9) and have now cloned and sequenced the principal alcohol dehydrogenase isozyme from this organism, the adhB gene.

*Z. mobilis* contains two isozymes for alcohol dehydrogenase which are readily distinguished on acrylamide gel zymograms, by ion-exchange chromatography (18, 39), and by their ability to oxidize butanol (20, 28). Although alcohol dehydrogenase II is the most abundant isozyme, both appear to contribute during fermentation (20, 28). Both isozymes have been purified, and the N-terminal amino acid sequences have been determined by polypeptide sequencing (28). The alcohol dehydrogenase I isozyme from *Z. mobilis* is a tetramer containing zinc with a monomeric molecular weight of between 34,000 and 40,000. The alcohol dehydrogenase II isozyme from *Z. mobilis* is reported to be somewhat smaller, a tetramer with a monomeric molecular weight between 31,000 and 38,000 (18, 20, 28, 36, 39). This isozyme is quite unusual, containing iron rather than zinc in its active site (28, 36). The alcohol dehydrogenase II isozyme is the most abundant alcohol dehydrogenase activity in *Z. mobilis* and has a high degree of specificity for ethanol as a substrate (20, 28, 39).

In this paper, we describe a novel indicator plate method for the direct detection of clones which express alcohol dehydrogenase. This technique has been used to clone the gene encoding alcohol dehydrogenase II (adhB) from *Z. mobilis*. This gene was sequenced, and the sites for transcriptional initiation were determined.

The invention of the subject application was disclosed in an article published in the Journal of Bacteriology, June, 1987, pp. 2591-2597.

BRIEF SUMMARY OF THE INVENTION

The gene which encodes alcohol dehydrogenase II (adhB) from *Zymomonas mobilis* was cloned in *Escherichia coli* as a 1.4-kilobase DNA fragment by using a novel indicator plate which directly detects the expression of this activity by recombinant colonies. The DNA sequence for this clone contained an open reading frame encoding a polypeptide of 383 amino acids, with a molecular weight of 40,141. Although this protein exhibited very little homology with other known alcohol dehydrogenases, the predicted amino acid composition was in excellent agreement with that reported for the purified alcohol dehydrogenase II protein from *Z. mobilis*. In *Z. mobilis*, the adhB gene was transcribed from tandem promoters which were separated by 100 base pairs and ended with a transcriptional terminator (13-base-pair palindrome). In *Escherichia coli*, only one of the *Z. mobilis* promoters was used, despite apparent similarity to the enteric consensus promoter. The adhB gene was transcribed at low levels in *E. coli* from the P2 promoter of *Z. mobilis* but was expressed well in *E. coli* under control of the lac promoter (approximately 0.25% of the total cell protein).

DETAILED DESCRIPTION OF THE INVENTION

Materials and Methods

Bacterial strains, plasmids, and growth conditions. The strains and plasmids used in this study are described in Table 1. *Z. mobilis* CP4 was grown in complex medium (29) at 30° C. without agitation. *E. coli* strains were grown at 37° C. in Luria broth (24) containing added carbohydrate only when indicated below. Solid media contained agar (15 g/liter). Transformants of *E. coli* were isolated and identified by using media containing ampicillin (50 mg/liter), chloramphenicol (40 mg/liter), and X-Gal (5-bromo-4-chloro-3-indolyl-β-D-galactoside; 20 mg/liter) and by using an aldehyde indicator plate.

BRIEF DESCRIPTION OF THE DRAWINGS

FIGS. 2-1, 2-2, 2-3, 2-4 and 2-5 is the DNA sequence and translated amino acid sequence of adhB from *Z. mobilis*.

Aldehyde indicator plates for the direct detection of clones producing alcohol dehydrogenase. Mixtures of pararosaniline and bisulfite are often referred to as Schiff reagent and have been widely used to detect aldehydes (22), to detect sugars on glycoproteins after periodic acid oxidation (14, 16), and in a broth test for organisms such as *Z. mobilis* which secrete aldehydes (11). These components have been incorporated into a solid medium which is relatively nontoxic and can be used to identify clones expressing enzymes which produce aldehydes.

Indicator plates were prepared by adding 8 ml of pararosaniline (2.5 mg/ml of 95% ethanol; not autoclaved) and 100 mg of sodium bisulfite (unsterilized dry powder) to 400-ml batches of precooled (45° C.) Luria agar lacking added carbohydrate. Most of the dye was immediately converted to the leuco form by reaction with the bisulfite (22) to produce a rose-colored medium which was dispensed into petri plates. Plates were stored at room temperature, away from fumes which contain aldehydes (cigarette smoke, many plastic containers, etc.) and light, both of which promote increased background color.

Ethanol diffuses into the *E. coli* cells, where it can be converted to acetaldehyde by alcohol dehydrogenase. The leuco dye serves as a sink, reacting with acetaldehyde to form a Schiff base which is intensely red (22). This reaction would be expected to shift the equilibrium for alcohol hydrogenase toward aldehyde production. The red product was still quite soluble and diffused into the surrounding agar.

TABLE 1

Plasmids and strains used

| Strain or plasmid | Relevant genotype | Source or reference |
|---|---|---|
| *Z. mobilis* CP4 | Prototroph | 29 |
| *E. coli* | | |
| TC4 | recA lacY | 4 |
| DH5α | lacI$^q$ΔlacZM15 recA | BRL[a] |
| JM101 | lacI$^q$ΔlacZM15 | BRL |
| Plasmids | | |
| pUC18 | bla lacI'Z'[b] | 40 |
| pLOI193 | cat mob$^+$ | 8 |
| pLOI284 | bla adhB | This study |
| pLOI285 | cat adhB | This study |
| pLOI286 | bla adhB | This study |
| pLOI287 | bla adhB | This study |

[a] Bethesda Research Laboratories.
[b] Incomplete lacI and incomplete lacZ.

Positive colonies were best visualized in low numbers (less than 20 positive colonies per plate containing 100 to 300 total colonies) after overnight incubation at 37° C. (with or without added antibiotics). Such colonies completely colored the plates after prolonged incubation. Active colonies appeared intensely red, with negative colonies ranging from white to medium shades of red, depending upon the level of background color in the plate, a function of indicator plate age and storage conditions. Fresh indicator plates were prepared no more than 2 days before use.

Figure 1A:
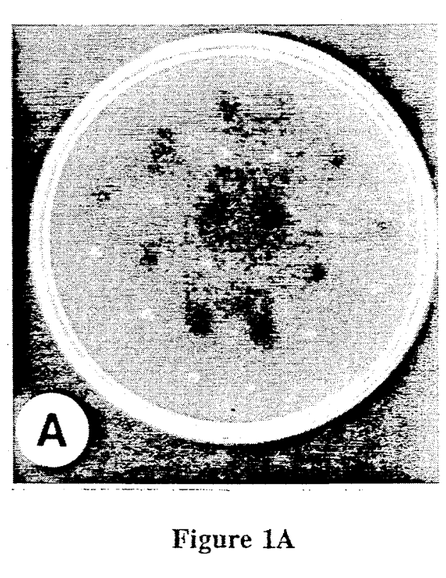
FIG. 1A shows positive colonies detected after 20 minutes to 2 hours at 37° C.

Colonies selected by antibiotic resistance were tested for alcohol dehydrogenase activity by using sterile toothpicks or applicator sticks to transfer cells to gridded aldehyde indicator plates. Positive clones were detected after 20 min to 2 h at 37° C. (FIG. 1A). During overnight or longer incubation, negative colonies were surrounded by a halo which was lighter than the background plate (FIG. 1B), presumably due to the consumption of aldehydes by the aldehyde dehydrogenase activity known to be present in *E. coli* (6). The relatively low levels of native alcohol dehydrogenase in *E. coli* (5) may contribute to the modest color development in negative clones during incubation.

The addition of glucose and other readily fermentable sugar resulted in sufficient aldehyde production to darken plates and produce red colonies with little diffusion of colored product. However, modifications of this plate assay can be used to screen for pyruvate decarboxylase activity (more intensely red with diffusion of pigment) by using glucose for growth or pyruvate instead of ethanol as a substrate.

Cloning of the adhB gene. Chromosomal DNA was isolated from *Z. mobilis* as described previously (4). This DNA was partially digested with Sau3A, and fragments of 5 to 7 kilobases (kb) were isolated by using a sucrose gradient (7). A *Z. mobilis* library was constructed by ligating these fragments into the BamHI site of the tetracycline resistance gene of pLOI193 (8). Ligated preparations were transformed into *E. coli* TC4 with selection for chloramphenicol resistance. Three ligations were used to construct the library. Each ligation yielded approximately 10,000 colonies, of which over 50% contained an insert. These original plates were scraped and transferred into centrifuge tubes, and the plasmid DNA was isolated by using the alkaline sodium dodecyl sulfate method (25). This DNA served as an amplified library and gene bank from which alcohol dehydrogenase clones were isolated as new transformants of strain TC4 on aldehyde indicator plates containing chloramphenicol. Alcohol dehydrogenase activity was confirmed by direct spectrophotometric assay by measuring the acetaldehyde-dependent oxidation of NADH.

Subclones were prepared by the ligation of fragments from purified plasmids into the vector pUC18 (40). These ligations were transformed into *E. coli* DH5α (Table 1) and plated on Luria agar containing ampicillin and X-Gal. Clones containing inserts (negative for β-galactosidase) were screened for alcohol dehydrogenase activity by picking onto aldehyde indicator plates. These were back-transformed into strain TC4 for further study.

Assay of alcohol dehydrogenase. Alcohol dehydrogenase activity was determined by measuring the acetaldehyde-dependent oxidation of NADH or by measuring the alcohol-dependent reduction of NAD$^+$ by using ethanol or butanol (28). Cell suspensions in buffer (0.1M Tris maleate, 1 mM dithiothreitol [pH 6.5]) were disrupted by the addition of lysozyme (0.5 mg/ml) and vigorous mixing with chloroform (0.025 ml of chloroform added to 0.2 ml of cell suspension). Activities are expressed as micromoles per minute per milligram of total cell protein. Cell protein was determined by using the method of Lowry et al. (23) with bovine serum albumin as a standard.

Acrylamide gel electrophoresis. Sodium dodecyl sulfate-polyacrylamide gel electrophoresis was performed as described previously (9). For zymograms of alcohol dehydrogenase isozymes, cells were disrupted with lysozyme and detergent (28) and separated on 7% polyacrylamide gels with a 3% stacking gel essentially as previously described (38). Alcohol dehydrogenase activity was visualized by using phenazine methosulfate and nitrotetrazolium blue (15).

DNA sequence analysis. The gene encoding alcohol dehydrogenase II from *Z. mobilis* was sequenced by the dideoxy method of Sanger et al. (35) as described previously (8). The entire sequence of the *Z. mobilis* DNA insert of pLOI284 was determined for both strands. Staggered deletions of about 175 base pairs (bp) each were prepared by opening the plasmid at one end of the insert, followed by timed digestions with the nuclease BAL 31 (25). The deletion fragments were digested with a second restriction enzyme, which cut at the opposite end of the insert, and subcloned into bacteriophage M13mp18 or M13mp19. In addition, the 402-bp DraI fragment of pLOI287 (immediately upstream of the sequence present in pLOI284) was sequenced in both directions by cloning into M13mp18. The sequence data were analyzed by using the programs of Pustell and Kafatos (32), obtained from International Biotechnologies, Inc., Beverly, Mass.

Analysis of transcriptional initiation sites. The 5' termini of the transcripts were mapped by the primer extension method (31). RNA isolation and mapping experiments were performed as described previously (9). The primer used for these experiments was synthesized by using an Autogen 500 oligonucleotide synthesizer (Millipore Corp., Bedford, Mass.) and was complementary to the noncoding strand of the adhB gene (3'-GCAGTTGCTTTACCC-5'), spanning bp 206 (3') to 220 (5'). The cDNA prepared in these experiments was compared to a sequence ladder generated with the same primer and the appropriate M13 clone containing the homologous DNA fragment.

Enzymes and chemicals. Restriction enzymes were obtained from International Biotechnologies. Avian myeloblastosis virus reverse transcriptase and the Klenow fragment of DNA polymerase I were obtained from Bethesda Research Laboratories, Inc., Gaithersburg, Md. Dideoxy- and deoxynucleotides were purchased from Pharmacia, Inc., Piscataway, N.J. Biochemicals, pararosaniline, and sodium bisulfite were purchased from Sigma Chemical Co., St. Louis, Mo. Radioactive compounds were obtained from New England Nuclear Corp., Boston, Mass.

Results

Figure 1B:
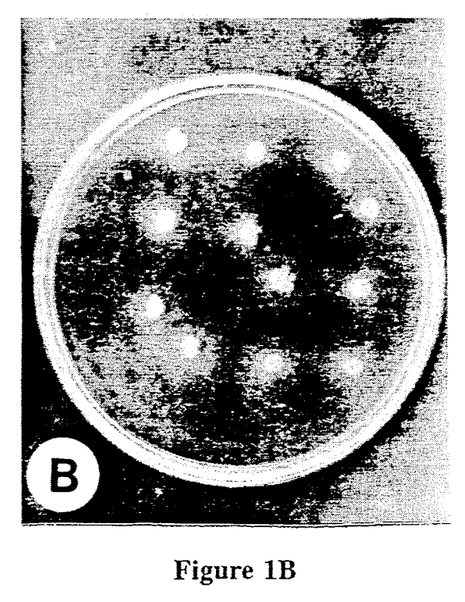
FIG. 1B shows negative colonies surrounded by a halo.

Cloning of the alcohol dehydrogenase II gene from Z. mobilis. A library of Z. mobilis genomic DNA in the broad host range vector pLOI193 (8) was transformed into E. coli TC4 and plated on aldehyde indicator plates containing chloramphenicol. More than 20,000 colonies were screened, and three positive clones were found, similar to those shown in FIG. 1. The presence of alcohol dehydrogenase was confirmed in the three clones by direct spectrophotometric assay. These clones appeared to be identical in that they contained inserts of 5.6 kb and were digested into identical fragments by EcoRV and DraI. One of these clones was designated pLOI285 and retained for further study.

The 5.6-kb Z. mobilis DNA fragment was mapped by using a variety of restriction endonucleases. The first subclone retaining a functional adhB gene was made by digestion of pLOI285 with EcoRV, followed by ligation of the fragments into the SmaI site of pUC18. This subclone, designated pLOI287, contained two EcoRV fragments (2.2 and 1.2 kb long). Both of these fragments were required to retain alcohol dehydrogenase activity. A subclone of pLOI287 was constructed by digestion with BstEII and EcoRI, followed by conversion of the staggered cuts to blunt ends by using the Klenow fragment of DNA polymerase I and self-ligation. This plasmid, designated pLOI286, was further shortened by subcloning the DraI fragments of the Z. mobilis insert DNA into the SmaI site of pUC18. This final construction was designated pLOI284 and contained the smallest pieces of Z. mobilis DNA which retained a functional alcohol dehydrogenase. It contained the two DraI fragments from pLOI286, 0.12 and 1.23 kb long, and retained a single, internal DraI site.

Sequence of the adhB gene from Z. mobilis. The sequence of the gene encoding alcohol dehydrogenase II in Z. mobilis is presented in FIG. 2. A single open reading frame of 1,149 bp was identified, corresponding to 383 amino acids (including the N-terminal methionine), with an aggregate molecular weight of 40,141. The N-terminal amino acid sequence of Z. mobilis for this protein has been previously reported (28) and is identical to that predicted by our sequence through the first 36 amino acids. The sequences differ at amino acid 37, which was reported by Neale et al. (28) to be a glycine but is a serine in our sequence and may represent a strain variation (single base change). Amino acids in positions 38 through 49 are in agreement with those determined by peptide sequencing (28). The predicted amino acid composition from our sequence is in excellent agreement with that reported by Wills et al. (39).

The coding region of adhB is preceeded by the sequence GAGG, a probable ribosome-binding site (10, 21) located 8 bp upstream from the start codon. This gene ends with a single stop codon, TAA. A 13-bp palindrome which resembles a procaryotic terminator (30, 34) is located 50 bp downstream from this stop codon. We confirmed that the palidrome acts as a terminator by inserting a promoterless tetracycline gene downstream, a construction which did not confer resistance to tetracycline. The sequence upstream from the ribosome-binding site of adhB is extremely A+T rich and contains several potential $-10$ and $-35$ regions, although most of these do not show the proper spacing to be considered homologous to the promoter consensus sequence described for E. coli (17, 34).

Expression of the adhB gene in E. coli. Z. mobilis contains two isozymes for alcohol dehydrogenase which can be readily distinguished by their ability to oxidize butanol and by their rates of migration on zymograms (20, 28, 39). By using these criteria, the activity produced in E. coli by clones containing pLOI286 and pLOI284 was identified as alcohol dehydrogenase II from Z. mobilis. Cell extracts rapidly oxidized ethanol but failed to oxidize butanol. On native gels, this activity migrated adjacent to alcohol dehydrogenase II from extracts of Z. mobilis (data not shown). Sodium dodecyl sulfate-polyacrylamide gels of extracts from Z. mobilis CP4 and E. coli TC4 containing pLOI284 were also examined. Strain TC4 containing pLOI284 exhibited an increase in protein in the region corresponding to 38,000 to 40,000 daltons, although this band was not cleanly resolved from native proteins (data not shown).

During the construction of pLOI284, only a single orientation of fragments in pUC18 was obtained, suggesting that the expression of adhB may be dependent upon the lac promoter in pUC18 for transcription. If a specific activity for pure enzyme of 170 U (28) is assumed, alcohol dehydrogenase II from Z. mobilis can be calculated to represent 0.25% of the total cellular protein in E. coli grown without glucose (Table 2). This activity was roughly halved by growth in the presence of glucose (Table 2), consistent with the adhB gene in pLOI284 being transcribed under the control of the lac promoter (12). In contrast, the level of activity expressed by strain TC4 containing pLOI286 was much lower and exhibited a smaller decline during growth with glucose.

Figure 3A:
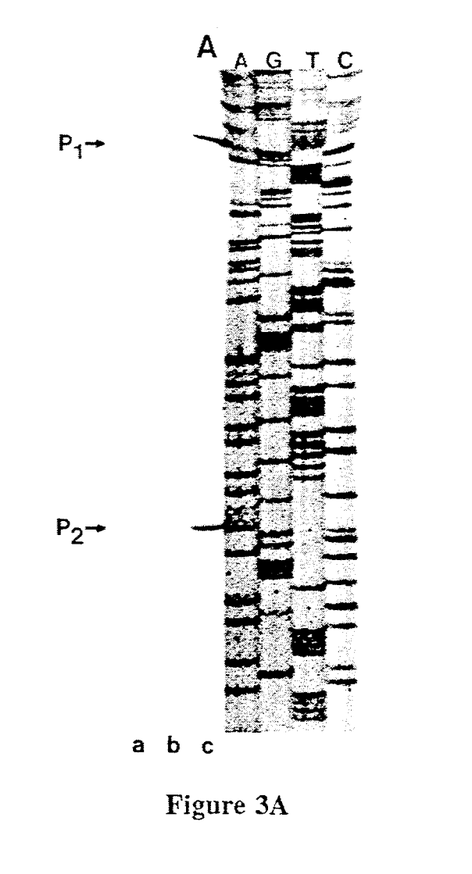
FIG. 3A shows comparisons to sequencing ladder from pLOI286.

Mapping of transcriptional initiation of adhB. The sites of transcriptional initiation were identified by primer extension analysis by using mRNA isolated from Z. mobilis CP4 during the logarithmic growth phase (FIG. 3A). Two prominent bands were evident and of equal intensity, indicating that transcription of adhB in Z. mobilis was initiated from two different promoters. The second of these, designated P2, was assigned as bp 1 (a thymidine) in FIG. 2 and is 177 bp upstream of the translational start codon. The other initiation site, designated P1, is also a thymidine and is located 277 bp upstream of the translational start codon.

Figure 3B:
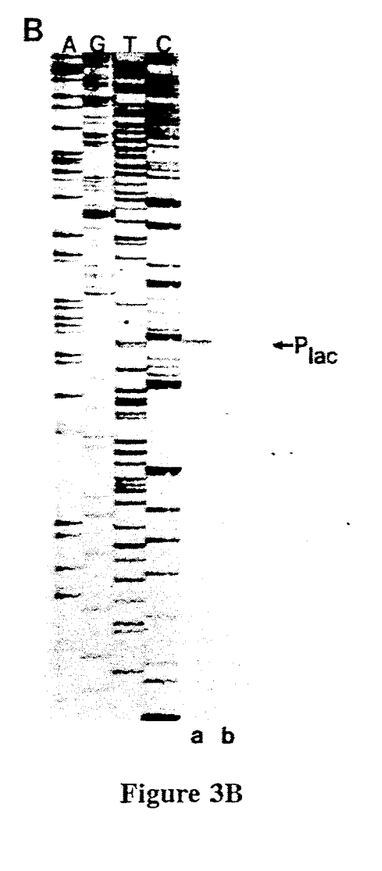
FIG. 3B shows comparisons to sequencing ladder from pLOI284.
Figure 21:
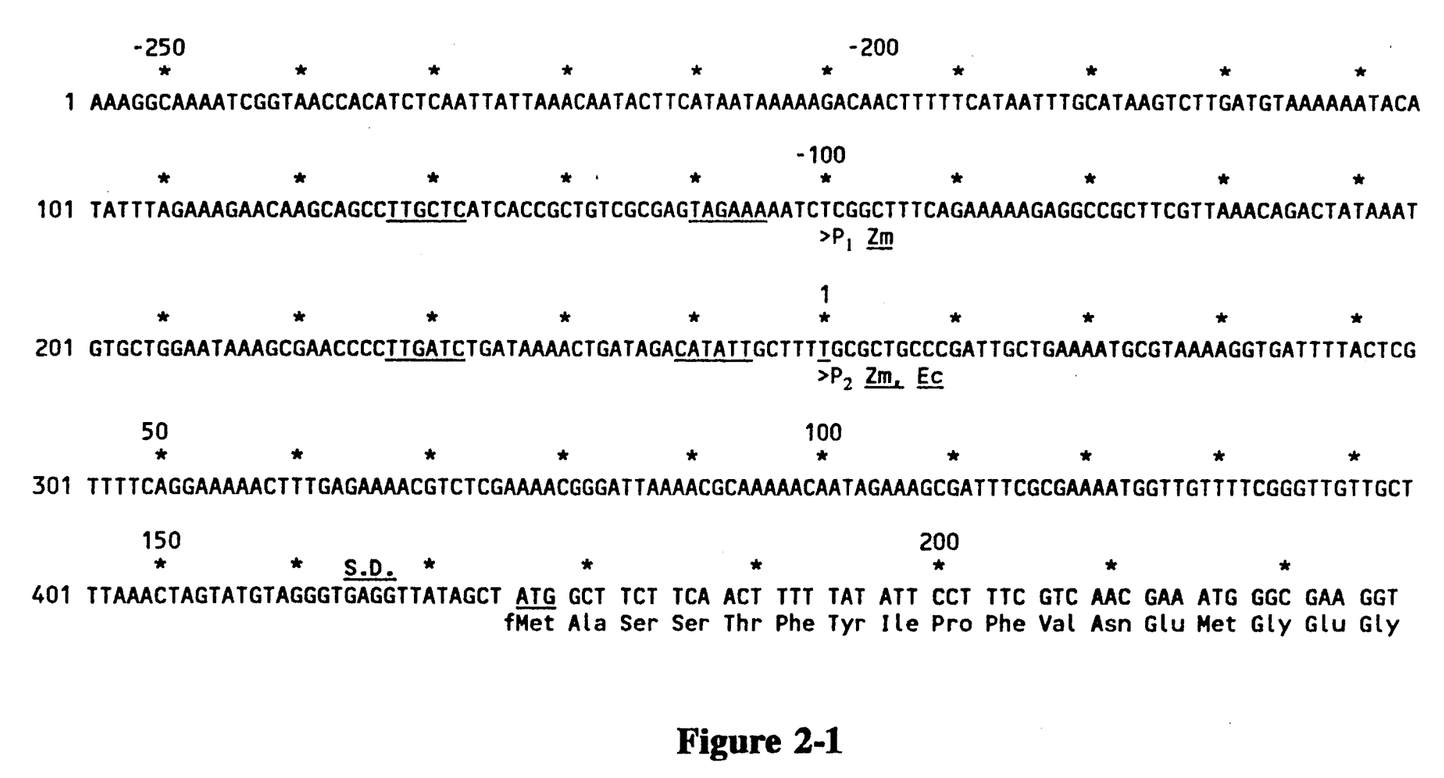
Figure 22:
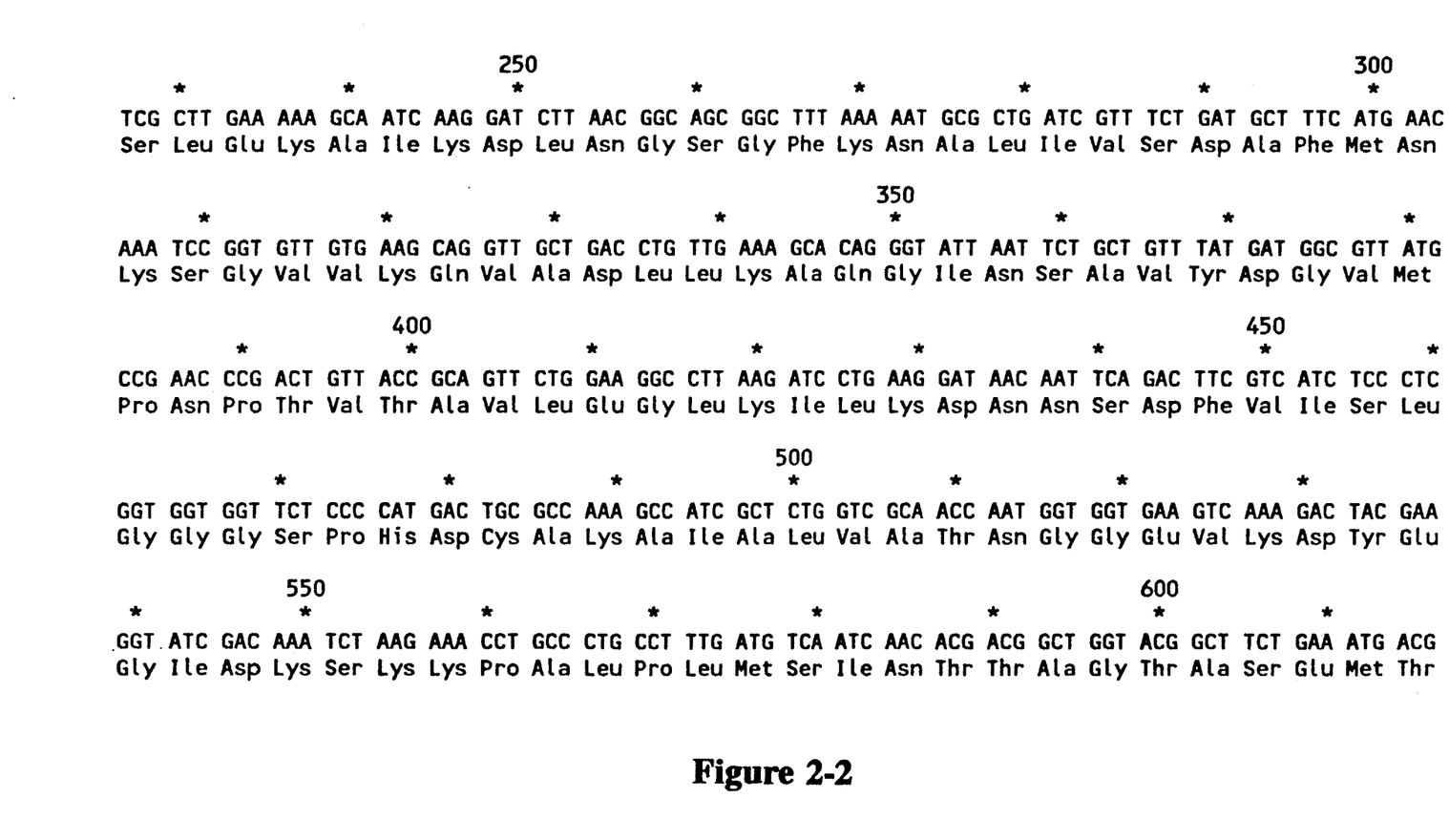
Figure 23:
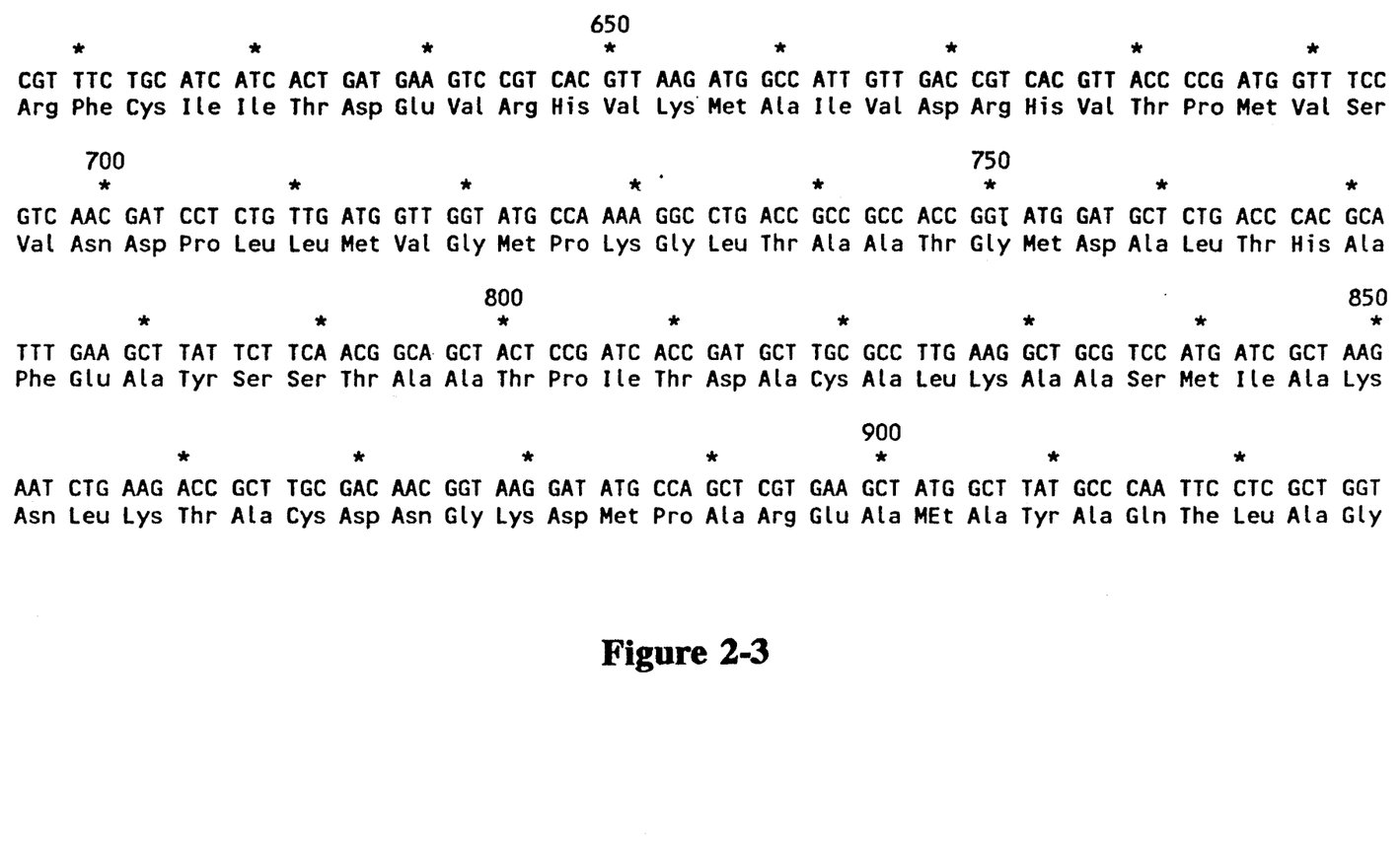
Figure 24:
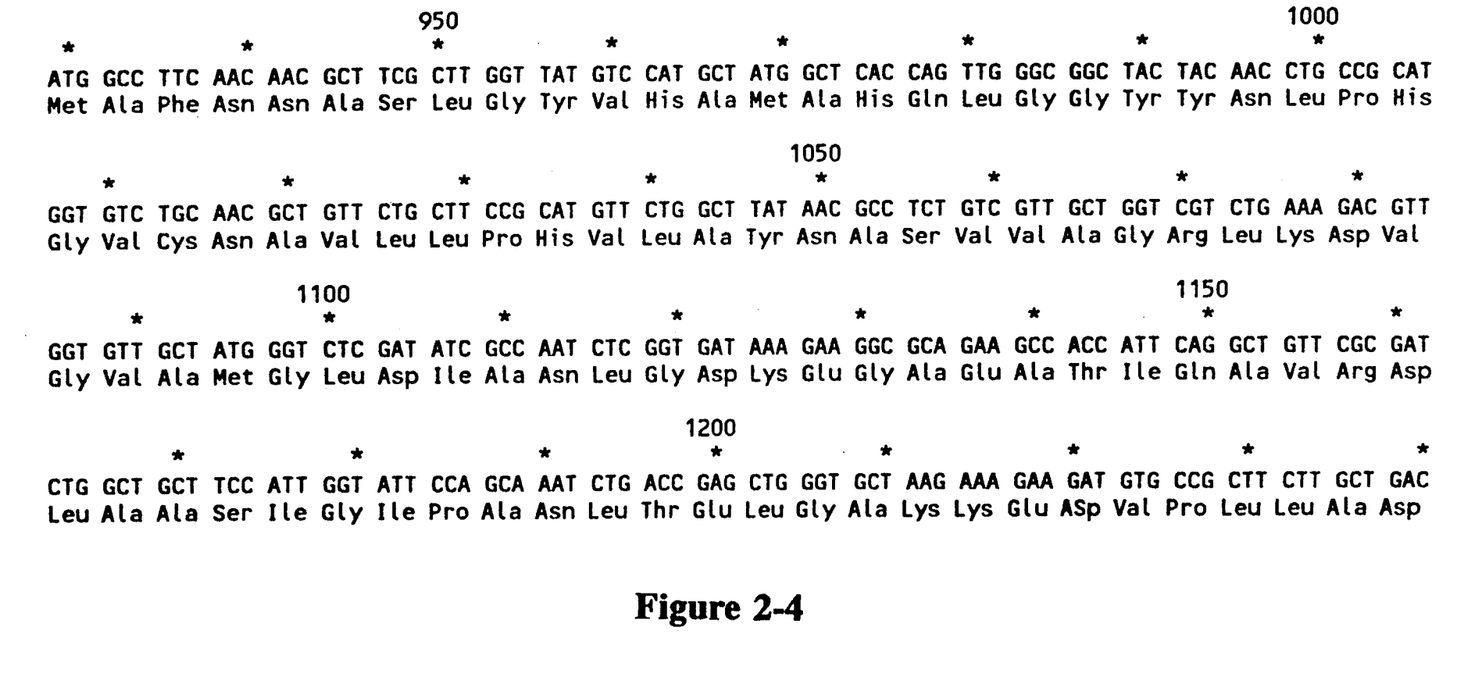
Figure 25:
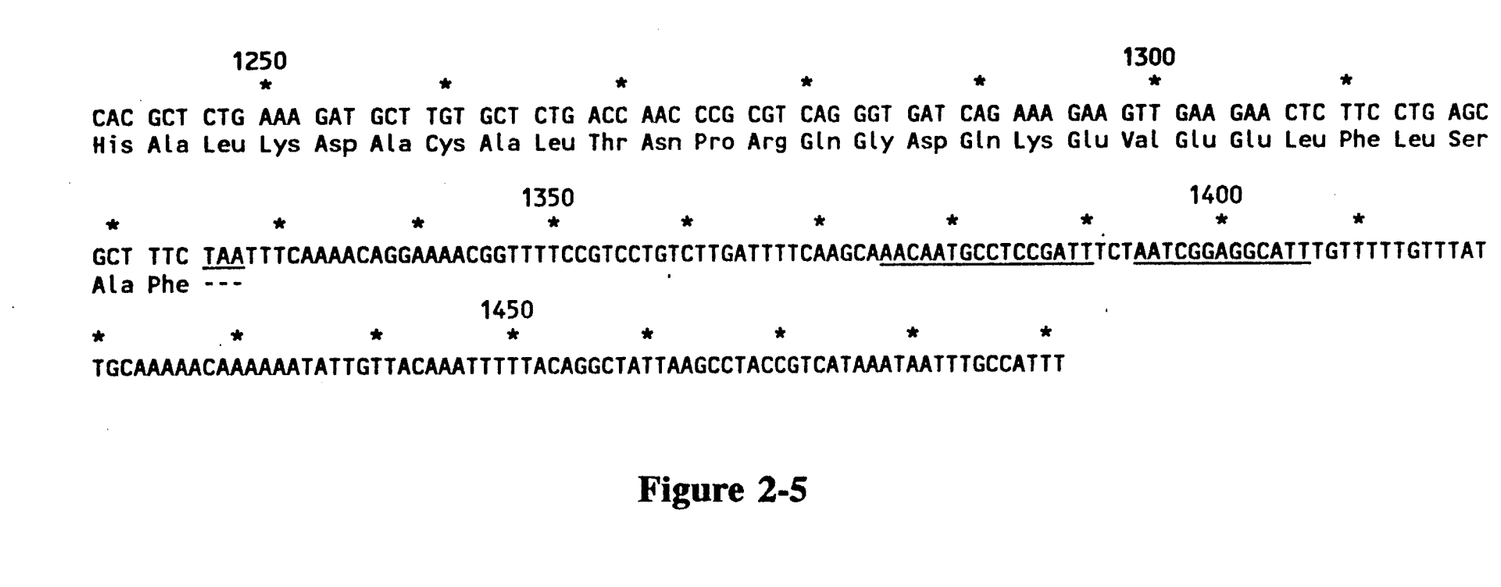

Primer extension experiments using mRNA from E. coli TC4 containing pLOI286 (carrying the entire promoter region of adhB) indicated a weak site of initiation directly adjacent to the thymidine used by Z. mobilis at P2 (FIG. 3A; visible with longer exposure). Strain TC4 did not appear to use P1. A similar experiment with strain TC4 carrying pLOI284, which contains a shortened adhB lacking both Z. mobilis promoters, exhibited a single site of transcriptional initiation from the lac promoter supplied by pUC18 (FIG. 3B).

Each of the tandem promoters used by Z. mobilis is similar to the consensus promoter sequence for E. coli (17, 34), although they differ from one another. The −10 region of P2 has the sequence CATATT, with four of six bases in common with the consensus sequence (17, 34). The −10 region of P1 contains the sequence TAGAAA, also with four of six bases matching the consensus sequence. The −35 regions of P2 and P1 are nearly homologous, with the sequences TTGATC and TTGCTC, respectively. The first shares four of six bases in common with the −35 consensus sequence, and the latter shares three of six bases. Both of

TABLE 2

Specific activity of alcohol dehydrogenase clones

| Plasmid[a] | Glucose[b] | Alcohol dehydrogenase ($\mu$mol/min per mg of total cell protein)[c] |
|---|---|---|
| pLOI284 | + | 0.18 |
| | − | 0.43 |
| pLOI286 | + | 0.08 |
| | − | 0.10 |
| No plasmid | + | 0.04 |
| | − | 0.05 |

[a]Plasmids contained in E. coli TC4.
[b]Cells were grown in Luria broth in the presence or absence of glucose (20 g/liter).
[c]Measured by acetaldehyde-dependent oxidation of NADH.

these promoters have the proper spacing of 17±1 bp between the −10 and −35 regions (17, 34).

Discussion

The adhB gene from Z. mobilis was transcribed from tandem promoters. This is not unexpected for an important, highly regulated gene and is not uncommon in other procaryotes (13, 26). However, Z. mobilis is obligately fermentative and requires alcohol dehydrogenase for the oxidation of NADH under all growth conditions. The Z. mobilis adhB promoter structure appears unusual in two ways. First, both of the adhB promoters were used by Z. mobilis during log-phase growth. Normally, tandem promoters are differentially expressed (3, 33). Tandem promoters of the adh gene from Drosophila melanogaster are expressed separately, at different stages of development (1). A second unusual feature of the tandem Z. mobilis promoters is the uncharacteristically long, untranslated 5'-mRNA leaders. The significance of such leaders is unknown.

The two adhB promoters of Z. mobilis were not used efficiently for expression in E. coli, although both share homology with the consensus promoter sequence of E. coli (17, 34). The P2 promoter of adhB was used to a limited extent, and the P1 promoter appeared to be unused by E. coli. The −35 regions of the two adhB promoters are nearly identical. It is likely that the differences between the two adhB promoters in the −10 region are important for utilization by E. coli and for the regulation of alcohol dehydrogenase II activity in Z. mobilis. High levels of alcohol dehydrogenase II are present in this obligately ethanologenic bacterium, although the proportions of the two isozymes have been reported to vary with growth conditions and at different stages of batch fermentation (20). In E. coli, transcription from the lac promoter was blocked in pLOI286 but not in pLOI284, although no palindromic sequences are evident in the additional upstream region of pLOI286 which could serve as transcriptional terminators.

The other enzyme required by Z. mobilis for the regeneration of NAD+, i.e., pyruvate decarboxylase, has also been cloned (2) and sequenced (9). The promoter for pdc is unused by E. coli but serves to express this gene at high levels during fermentation in Z. mobilis. No sequence homology was evident between the promoters of pdc and adhB (data not shown). The predicted peptide sequence of Z. mobilis alcohol dehydrogenase II exhibited no appreciable homology to reported sequences for alcohol dehydrogenases from maize, yeasts, mammals, or D. melanogaster. A small region of possible homology in the amino end with yeasts has been described previously (28). The apparent lack of homology is consistent with the unusual nature of the Z. mobilis alcohol dehydrogenase II enzyme, reported to be the only alcohol dehydrogenase to contain iron rather than zinc (36).

The transcription of both adhB (pLOI284) and pdc (pLOI276; 9) was initiated from the lac promoter (derivatives of pUC18) in E. coli TC4. However, the level of pyruvate decarboxylase produced in strain TC4 was eightfold higher than the level of alcohol dehydrogenase II when compared as a percentage of total cellular protein. Such differences in levels of enzyme may reflect differences in mRNA stability, protein stability, or efficiency of translation (19). In Z. mobilis, alcohol dehydrogenase (both isozymes) also represents a smaller fraction of cellular protein than does pyruvate decarboxylase, although both activities are abundant (18).

The protein encoded by the gene of the invention can be used to convert ethanol, a low value product of fermentation, to acetaldehyde, a product of higher value. This conversion can be done by contacting organisms expressing the subject protein with ethanol in the presence of air. This is shown in FIG. 1. Acetaldehyde is a known flavoring agent in foods and beverages.

Literature Cited

1. Benyajati, C., N. Spoere, H. Haymerle, and M. Ashburner. 1983. The messenger RNA for alcohol dehydrogenase in *Drosophila melanogaster* differs in its 5' end in different developmental stages. Cell 33:125-133.
2. Brau, B., and H. Sahm. 1986. Cloning and expression of the structural gene for pyruvate decarboxylase of *Zymomonas mobilis*. Arch. Microbiol. 144:296-301.
3. Busby, S., H. Aiba, and B. DeCrombrugghe. 1982. Mutations in the *Escherichia coli* operon that define two promoters and the binding site of the cyclic AMP receptor protein. J. Mol. Biol. 154:211-227.
4. Byun, M. O.-K., J. B. Kaper, and L. O. Ingram. 1986. Construction of a new vector for the expression of foreign genes in *Zymomonas mobilis*. J. Ind. Microbiol. 1:9-15.
5. Clark, D., and J. E. Cronan, Jr. 1980. *Escherichia coli* mutants with altered control of alcohol dehydrogenase and nitrate reductase. J. Bacteriol. 141:177-183.
6. Clark, D. P., and J. E. Cronan, Jr. 1981. Acetaldehyde coenzyme A dehydrogenase of *Escherichia coli*. J. Bacteriol. 144:179-184.
7. Clark-Curtiss, J. E., W. R. Jacobs, M. A. Docherty, L. R. Ritchie, and R. Curtiss III. 1985. Molecular analysis of DNA and construction of genomic libraries of *Mycobacterium leprae.* J. Bacteriol. 161:1093–1102.

8. Conway, T., M. O.-K. Byung, and L. O. Ingram. 1987. Expression vector for *Zymomonas mobilis.* Appl. Environ. Microbiol. 53:235–241.

9. Conway, T., Y. A. Osman, J. I. Konnan, E. M. Hoffman, and L. O. Ingram. 1987. Promoter and nucleotide sequences of the *Zymomonas mobilis* pyruvate decarboxylase. J. Bacteriol. 169:949–954.

10. DeBoer, H. A., L. J. Comstock, A. Hui, E. Wong, and M. Vasser. 1983. A hybrid promoter and portable Shine-Dalgarno regions of *Escherichia coli.* Biochem. Soc. Symp. 48:233–244.

11. Dennis, R. T., and T. W. Young. 1982. A simple and rapid method for detection of subspecies of *Zymomonas mobilis.* J. Inst. Brew. 88:25–29.

12. Dickson, R. C., J. Albeson, W. M. Barnes, and W. S. Reznikoff. 1975. Genetic regulation: the lac control region. Science 187:27–35.

13. Doi, R. H., and L.-F. Wang. 1986. Multiple procaryotic ribonucleic acid polymerase sigma factors. Microbiol. Rev. 50:227–243.

14. Fairbanks, G., T. L. Steck, and D. F. H. Wallach. 1971. Electrophoretic analysis of the major polypeptides of the human erythrocyte membrane. Biochemistry 10:2606–2617.

15. Fowler, P. W., A. J. S. Ball, and D. E. Griffiths. 1972. The control of alcohol dehydrogenase isozyme synthesis in *Saccharomyces cerevisiae.* Can. J. Biochem. 50:35–43.

16. Gander, J. E. 1984. Gel protein stains: glycoproteins. Methods Enzymol. 104:447–450.

17. Hawley, D. K., and W. R. McClure. 1983. Compilation and analysis of *Escherichia coli* promoter DNA sequences. Nucleic Acids Res. 11:2237–2255.

18. Hoppner, T. C., and H. W. Doelle. 1983. Purification and kinetic characteristics of pyruvate decarboxylase and ethanol dehydrogenase from *Zymomonas mobilis* in relation to ethanol production. Eur. J. Appl. Microbiol. Biotechnol. 17:152–157.

19. Ikemura, T. 1981. Correlation between the abundance of *Escherichia coli* transfer RNAs and the occurrence of the respective codons in its protein genes: a proposal for a synonomous codon choice that is optimal for the *E. coli* translational system. J. Mol. Biol. 151:389–409.

20. Kinoshita, S., T. Kakizono, K. Kadota, K. Das, and H. Taguchi. 1985. Purification of two alcohol dehydrogenases from *Zymomonas mobilis* and their properties. Appl. Microbiol. Biotechnol. 22:249–254.

21. Kozak, M. 1983. Comparison of initiation of protein synthesis in procaryotes, eucaryotes, and organelles. Microbiol. Rev. 47:1–45.

22. Lillie, R. D. 1977. H. J. Conn's biological stains, 9th ed., p. 259–266. The Williams & Wilkins Co., Baltimore.

23. Lowry, O. H., N. J. Rosebrough, A. L. Farr, and R. J. Randall. 1951. Protein measurement with the Folin phenol reagent. J. Biol. Chem. 193:265–275.

24. Luria, S. E., and M. Delbruck. 1943. Mutations of bacteria from virus sensitivity to virus resistance. Genetics 28:491–511.

25. Maniatis, T., E. F. Fritsch, and J. Sambrook. 1982. Molecular cloning: a laboratory manual. Cold Spring Harbor Laboratory, Cold Spring Harbor, N.Y.

26. McClure, W. R. 1985. Mechanism and control of transcription initiation in prokaryotes. Annu. Rev. Biochem. 54:171–204.

27. Montenecourt, B. S. 1985. Zymomonas, a unique genus of bacteria, p. 261–289. In A. L. Demain and N. A. Soloman (ed.), Biology of industrial microorganisms. Benjamin-Cummings Publishing Co., Menlo Park, Calif.

28. Neale, A. D., R. K. Scopes, J. M. Kelly, and R. E. H. Wettenhall. 1986. The two alcohol dehydrogenases of *Zymomonas mobilis*: purification by differential dye ligand chromatography, molecular characterization and physiological role. Eur. J. Biochem. 154:119–124.

29. Osman, Y. A., and L. O. Ingram. 1985. Mechanisms of ethanol inhibition of fermentation in *Zymomonas mobilis* CP4. J. Bacteriol. 164:173–180.

30. Platt, T. 1986. Transcription termination and the regulation of gene expression. Annu. Rev. Biochem. 55:339–372.

31. Proudfoot, N. J., M. H. M. Shander, J. L. Manley, M. L. Gefter, and T. Maniatis. 1980. Structure and in vitro transcription of human globin genes. Science 209:1329–1336.

32. Pustell, J., and F. C. Kafatos. 1984. A convenient and adaptable package of computer programs for DNA and protein sequence management, analysis, and homology determination. Nucleic Acids Res. 12:643–655.

33. Reitzer, L. J., and B. Magasanik. 1985. Expression of glnA in *Escherichia coli* at tandem promoters. Proc. Natl. Acad. Sci. USA 82:1979–1983.

34. Rosenberg, M., and D. Court. 1979. Regulatory sequences involved in the promotion and termination of RNA transcription. Annu. Rev. Genet. 13:319–353.

35. Sanger, F., S. Nicklen, and A. R. Coulson. 1977. DNA sequencing with chain terminating inhibitors. Proc. Natl. Acad. Sci. USA 74:5463–5467.

36. Scopes, R. K. 1983. An iron-activated alcohol dehydrogenase. FEBS Lett. 156:303–306.

37. Swings, J., and J. De Ley. 1977. The biology of Zymomonas. Bacteriol. Rev. 41:1–46.

38. Williamson, V. M., J. Bennetzen, and E. T. Young. 1980. Isolation of the structural gene for alcohol dehydrogenase by genetic complementation in yeast. Nature (London) 283:214–216.

39. Wills, C., P. Kratofil, D. Londo, and T. Martin. 1981. Characterization of the two alcohol dehydrogenases of *Zymomonas mobilis.* Arch. Biochem. Biophys. 210:775–785.

40. Yanisch-Perron, C., J. Vieir, and J. Messing. 1985. Improved M13 phase cloning vectors and host strains: nucleotide sequence of the M13mp18 and M13mp19 vectors. Gene 33: 103–119.

We claim:

1. An isolated DNA fragment encoding bacterial alcohol dehydrogenase which has an amino acid sequence as shown in FIG. 2.

* * * * *

UNITED STATES PATENT AND TRADEMARK OFFICE
CERTIFICATE OF CORRECTION

PATENT NO. : 5,162,516

DATED : November 10, 1992

INVENTOR(S) : Lonnie O. Ingram, Tyrrell Conway

It is certified that error appears in the above-identified patent and that said Letters Patent is hereby corrected as shown below:

Column 1: line 23: "(27,37) Z. mobilis" should read --"(27,37). Z. mobilis--
Column 3: line 8: "hydrogenase" should read --dehydrogenase--.
Column 4: line 68: "experiments was" should read --experiments were--.

Throughout patent "adhB" should be italicized.

Signed and Sealed this

Twelfth Day of October, 1993

Attest:

BRUCE LEHMAN

Attesting Officer

Commissioner of Patents and Trademarks